(12) United States Patent
Choi

(10) Patent No.: US 9,011,793 B2
(45) Date of Patent: Apr. 21, 2015

(54) BLOOD GLUCOSE MONITORING SYSTEM, STRIP ACCOMMODATION DEVICE, STRIP STORAGE DEVICE, AND AUTOMATED BLOOD COLLECTION DEVICE

(76) Inventor: In Sang Choi, Anyang-si (KR)

( * ) Notice: Subject to any disclaimer, the term of this patent is extended or adjusted under 35 U.S.C. 154(b) by 355 days.

(21) Appl. No.: 13/217,829

(22) Filed: Aug. 25, 2011

(65) Prior Publication Data
US 2011/0313267 A1    Dec. 22, 2011

Related U.S. Application Data

(63) Continuation of application No. PCT/KR2011/001037, filed on Feb. 16, 2011.

(30) Foreign Application Priority Data

| Feb. 16, 2010 | (KR) | ......................... 10-2010-0013670 |
| Feb. 17, 2010 | (KR) | ......................... 10-2010-0014325 |
| Jan. 4, 2011 | (KR) | ......................... 10-2011-0000621 |
| Feb. 16, 2011 | (KR) | ......................... 10-2011-0013872 |
| Feb. 16, 2011 | (KR) | ......................... 10-2011-0013875 |

(51) Int. Cl.
| A61B 5/05 | (2006.01) |
| G01N 31/22 | (2006.01) |
| G01N 33/52 | (2006.01) |
| G01N 35/00 | (2006.01) |
| A61B 5/145 | (2006.01) |

(52) U.S. Cl.
CPC ................................ *A61B 5/14532* (2013.01)

(58) Field of Classification Search
None
See application file for complete search history.

(56) References Cited

U.S. PATENT DOCUMENTS

| 2003/0191415 A1* | 10/2003 | Moerman et al. ............ 600/584 |
| 2004/0127819 A1* | 7/2004 | Roe .............................. 600/583 |
| 2006/0155317 A1* | 7/2006 | List ............................... 606/181 |
| 2009/0098018 A1* | 4/2009 | Bainczyk et al. ............ 422/68.1 |
| 2010/0222703 A1* | 9/2010 | Takashima et al. ........... 600/583 |

FOREIGN PATENT DOCUMENTS

WO    WO 2009011137 A1 *   1/2009

* cited by examiner

*Primary Examiner* — Jill Warden
*Assistant Examiner* — Julie Tavares
(74) *Attorney, Agent, or Firm* — NSIP Law

(57) ABSTRACT

The present invention relates to a blood glucose monitoring system, a strip accommodation device, a strip storage device, and an automated blood collection device, wherein the blood glucose monitoring system has the strip accommodation device formed integrally therewith, the strip accommodation device being configured to convert a rotary motion of a cover of an operating member into an upward linear motion and to eject one of a plurality of strips through an ejection hole, thereby easily storing the strips therein, preventing the contamination of the strips from the foreign matters like outside moisture, and accurately and easily measuring the concentration of the glucose in the blood.

29 Claims, 11 Drawing Sheets

BLOOD GLUCOSE MONITORING SYSTEM, STRIP ACCOMMODATION DEVICE, STRIP STORAGE DEVICE, AND AUTOMATED BLOOD COLLECTION DEVICE

CROSS REFERENCE TO RELATED APPLICATIONS

This application is a continuation of International Patent Application No. PCT/KR2011/001037, filed on Feb. 16, 2011, which claims the benefit of Korean Patent Application No. 10-2010-0013670, filed on Feb. 16, 2010, Korean Patent Application No. 10-2010-0014325 filed on Feb. 17, 2010, Korean Patent Application No. 10-2011-0000621, filed on Jan. 4, 2011, Korean Patent Application No. 10-2011-0013872, filed on Feb. 16, 2011, and Korean Patent Application No. 10-2011-0013875 filed on Feb. 16, 2011, in the Korean Intellectual Property Office, the entire disclosures of which are incorporated herein by reference for all purposes.

BACKGROUND OF THE INVENTION

1. Field of the Invention

The present invention relates to a blood glucose monitoring system, and more particularly, to a blood glucose monitoring system, a strip accommodation device, a strip storage device, and an automated blood collection device that are configured to automatically eject strips for measuring blood glucose by means of simple opening or sliding of an operating member, thereby improving the storage quality and safety of the strips and the conveniences in use.

2. Background of the Related Art

As patients with diabetics, which is one of modern adult diseases, have been remarkably increased, portable and simple blood glucose monitors are required to obtain blood glucose data for the treatment and care of the diabetics. The blood glucose data is obtained by measuring the concentration of the glucose contained in the blood. Conventional Methods for measuring the blood glucose include a method based on the reduction property of glucose, a method by the direction reaction of glucose in an acid condition, and a method by the enzyme reaction of glucose, and alternatively, clinical medicine tests are carried out by collecting blood from a finger or toe or by using color reaction relying on the concentration of the glucose in the blood so as to measure a degree of the color and to calculate the measured color degree into a blood glucose level.

A conventional portable blood glucose monitor has a large-sized body and stores a blood collector, blood collection needles, and strips in separate cases, so that while it is being carried by a measurer or it is being stored in the cases, some components may be lost frequently. Typically, the strip case for storing the strips has a generally bulky cylindrical shape.

If even one of the components of the blood glucose monitor is lost, it is difficult to perform the blood glucose monitoring, and therefore, it is very inconvenient for the measurer who should measure his blood glucose at any time to carry the blood glucose monitor to him and to use it.

Especially, the blood glucose measurement is not performed accurately by the contamination of the strip caused by the moisture or foreign matters of the measurer's hand.

So as to check the glucose in the body, on the other hand, the blood collector is generally restored to its original position by means of an elastic force of a spring after blood collection.

That is, after a cap is separated from the blood collector, a separate blood collection needle is inserted into an insertion hole, and next, a protection cap is removed from the blood collection needle. Then, the cap of the blood collector is assembled again, and if a button on the blood collector is pressed, the blood collection needle is descended by means of the driving of a spring and is then inserted in the body.

After that, the cap of the blood collector is separated and the protection cap of the blood collection needle is assembled again. Next, the blood collection needle is removed from the insertion hole.

Therefore, the blood collector should be always carried along with the blood collection needle, which makes it inconvenient in use, and further, it is very inconvenient to manually insert the blood collection needle into the insertion hole.

SUMMARY OF THE INVENTION

Accordingly, the present invention has been made in view of the above-mentioned problems occurring in the prior art, and it is an object of the present invention to provide a blood glucose monitoring system having a strip accommodation device formed integrally therewith to convert a rotary motion of a cover into an upward linear motion and to eject one of a plurality of strips through an ejection hole, thereby allowing the strips to be easily accommodated in the strip accommodation device, preventing the strips from being contaminated by foreign matters like outside moisture, and accurately and easily performing the measurement of concentration of glucose.

It is another object of the present invention to provide a blood glucose monitoring system having a strip accommodation device formed integrally therewith to eject one of a plurality of strips through an ejection hole in accordance with a linear motion of a slide type cover mounted on one side surface of the blood glucose monitoring system, thereby allowing the strips to be easily kept in the strip accommodation device, preventing the strips from being contaminated by foreign matters like outside moisture, and accurately and easily performing the measurement of concentration of glucose.

It is still another object of the present invention to provide an automated blood collection device that is configured to guide and insert a blood collection needle into an insertion groove by means of a blood collection needle guide member, to move the inserted blood collection needle downwardly and to be fixed by means of a blood collection needle fixation member, to escape the blood collection needle from the insertion groove by means of a blood collection needle ejection member rotated by a given angle and to be then ejected to the outside after the blood collection has been finished, such that all of the processes of inserting and ejecting the blood collection needle are automatically carried out, thereby performing the blood collection in easier and more convenient manners and substantially improving the conveniences in the blood glucose measurement.

To accomplish the above objects, there is provided a blood glucose monitoring system including: an automated blood collection device; a strip accommodation device formed integrally with a blood glucose measurement device so as to convert a rotary motion generated by the manipulation of a measurer into an upward linear motion and to automatically eject one of a plurality of strips through an ejection hole formed thereon; and the blood glucose measurement device adapted to measure the concentration of glucose in the collected blood by means of the strip ejected from the strip accommodation device.

Desirably, the blood glucose monitoring system further includes a strip storage device detachably mounted thereon through an opening formed at a given position of the strip accommodation device and having the plurality of strips accommodated thereinto in such a manner as to convey the strip not used yet to the ejection hole.

Desirably, the strip accommodation device includes: a housing adapted to contain the plurality of strips arranged serially to collect blood thereon; an operating member disposed on the outer surface of the housing in such a manner as to be rotated by a first angle by means of the manipulation of a measurer at the time of measuring blood glucose; a first conveying member disposed on a given position in the housing and adapted to convert the rotary motion by the first angle of the operating member into an upward linear motion so as to convey one of the plurality of strips upwardly; and a second conveying member disposed on a given position in the housing in such a manner as to have one side opposite to the ejection hole formed on the housing so as to convey the strip not used yet to the ejection hole area.

Desirably, the operating member includes a folder type cover rotated by the first angle around a rotary shaft thereof in accordance with the manipulation of the measurer for blood glucose measurement.

Desirably, the first conveying member includes: a lever rotated by the rotation of the operating member and having a protrusion formed at the opposite position to the rotary shaft of the operating member; and a carriage adapted to be conveyed upwardly by means of the movement of the protrusion of the lever along a guide groove through the rotation of the lever and having a projection adapted to forcedly eject the strip positioned at the ejection hole area.

Desirably, the first conveying member further includes a plurality gears disposed on the rotary shaft of the operating member in such a manner as to be rotated by means of the rotation of the operating member and to transmit the rotary motion of the operating member to the lever.

Desirably, the length of the strip is set to be inversely proportional to the length of the lever.

Desirably, the second conveying member includes: a guide adapted to convey the strip not used yet to empty space after the strip has been ejected through the ejection hole; and an elastic module adapted to supply a given elastic force to the guide so as to allow the strip not used yet to be conveyed to the ejection hole area.

Desirably, the operating member is rotated by a second angle larger than the first angle to move the first conveying member upwardly and to completely eject the used strip to the outside.

Desirably, the operating member has a locking projection formed at the end thereof so as to seal the ejection hole after the blood glucose measurement has been finished, and the housing has a locking groove formed at a given position thereof so as to insert the locking projection of the operating member thereinto.

Desirably, the strip accommodation device includes: a housing adapted to contain the plurality of strips arranged serially to collect blood thereon; an operating member disposed on the outer surface of the housing in such a manner as to be opened at one side thereof to insert the housing into the inside thereof and adapted to be rotated by a given angle around a rotary shaft disposed on the outer surface of the housing; a first conveying member disposed on a given position in the housing and adapted to convert the rotary motion of the operating member into an upward linear motion so as to eject the strip through the ejection hole to the outside; and a second conveying member disposed on a given position in the housing in such a manner as to have one side opposite to the ejection hole formed on the housing so as to convey the strip not used yet to the ejection hole area.

Desirably, the operating member has a cover formed integrally therewith so as to seal the ejection hole when rotated in the opposite direction to the ejection direction of the strip after the used strip has been removed.

Desirably, the first conveying member includes: a lever rotated by the rotation of the operating member and having a protrusion formed at the opposite position to the rotary shaft of the operating member; and a carriage adapted to be conveyed upwardly by means of the movement of the protrusion of the lever along a guide groove through the rotation of the lever and having a projection adapted to forcedly eject the strip positioned at the ejection hole area.

Desirably, the first conveying member further includes: a gear module adapted to convert the rotary motion of the operating member into an upward linear motion; and the carriage adapted to be moved upwardly by means of the gear module so as to eject the strip through the ejection hole.

Desirably, the second conveying member includes: a guide adapted to convey the strip not used yet to empty space after the strip has been ejected through the ejection hole; and an elastic module adapted to supply a given elastic force to the guide so as to allow the strip not used yet to be conveyed to the ejection hole area.

Desirably, the housing further includes a moisture remover disposed at a given position therein so as to remove moisture therefrom.

Desirably, the cover of the operating member has a locking projection formed at the inside thereof so as to lock the cover to the housing, and the housing has a locking groove formed to insert the locking projection of the cover thereinto.

Desirably, the housing has a slot formed at a given position thereof so as to allow the blood glucose monitoring system to be carried along the measurer.

Desirably, the strip accommodation device includes: a housing adapted to contain the plurality of strips arranged serially to collect blood thereon; an operating member disposed on the outer surface of the housing in such a manner as to be slid by means of the manipulation of the measurer to cause a downward linear motion therefrom; a first conveying member disposed on a given position in the housing and adapted to convert the downward linear motion of the operating member into a rotary motion so as to convey one of the plurality of strips upwardly; and a second conveying member disposed on a given position in the housing in such a manner as to have one side opposite to the ejection hole formed on the housing and adapted to convey the strip not used yet to the ejection hole area.

Desirably, the operating member has a slide type cover adapted to be slid downwardly for the blood glucose measurement and having a rack gear disposed at a given position on the inner surface thereof.

Desirably, the slide type cover further has a guide rib formed at a given position on the inner surface thereof so as to prevent the escape thereof from the housing during the sliding operation.

Desirably, the first conveying member includes: a pinion gear rotated while being engaged with the rack gear of the operation member; a lever disposed on the rotary shaft of the pinion gear in such a manner as to be rotated by the rotation of the pinion gear and having a protrusion formed at the opposite position to the rotary shaft of the pinion gear; and a carriage adapted to be conveyed upwardly by means of the movement of the protrusion of the lever along a guide groove through the rotation of the lever and having a projection adapted to forcedly eject the strip positioned at the ejection hole area.

Desirably, the strip accommodation device further includes a sealing member adapted to be rotated by means of the rotation of the first conveying member so as to open and close the ejection hole.

Desirably, the sealing member includes: a cam gear adapted to be rotated by means of the rotation of the pinion gear of the first conveying member; and a sealing lever coupled on the rotary shaft of the cam gear in such a manner as to rotated by a given angle in accordance with the rotation of the cam gear and to open and close the ejection hole.

Desirably, the second conveying member includes: a guide adapted to convey the strip not used yet to empty space after the strip has been ejected through the ejection hole; and an elastic module adapted to supply a given elastic force to the guide so as to allow the strip not used yet to be conveyed to the ejection hole area.

Desirably, the operating member moves the first conveying member upwardly in accordance with the sliding position of the cover so as to eject the used strip to the outside.

Desirably, the automated blood collection device includes: a blood collection needle insertion member having an insertion groove having an opened semicircular portion and adapted to insert a blood collection needle thereinto; a rotary member adapted to be rotated by receiving a rotary force from a motor; a blood collection needle guide member adapted to convert a rotary motion of the rotary member into upward and downward motions around a fixing shaft and to thus convert the converted upward and downward motions into left and right motions so as to guide the blood collection needle to the insertion groove; a blood collection needle fixation member adapted to convert the rotary force of the rotary member into upward and downward motions so as to convey the blood collection needle downwardly and fix the blood collection needle thereto and to convey the blood collection needle upwardly after blood collection has been finished; and a blood collection needle ejection member adapted to be rotated by a given angle around the fixing shaft by receiving the rotary motion of the rotary member so as to allow the blood collection needle used for the blood collection to be escaped from the insertion groove.

Desirably, the automated blood collection device further includes a fixing cam adapted to be moved along a groove formed on the underside cross section of the rotary member so as to fix the fixing shaft to the rotary member.

Desirably, the blood collection needle guide member includes: a guide cam adapted to be moved along a groove formed along the lower outer periphery of the rotary shaft of the rotary member in such a manner as to perform upward and downward motions around the fixing shaft; a guide transmitter disposed on the other side of the guide cam so as to transmit the upward and downward motions of the guide cam; and a guide lever adapted to convert the upward and downward motions of the guide cam received from the guide transmitter into left and right motions around a rotary shaft thereof so as to guide the blood collection needle to the insertion groove.

Desirably, the blood collection needle includes: a conveying shaft having one side inserted into a groove formed on the blood collection needle ejection member and the other side conveyed downwardly so as to fix the blood collection needle by means of the blood collection needle fixation member; and a locking groove fixedly formed at a given position of the conveying shaft in such a manner as to be lockedly coupled to the blood collection needle fixation member.

Desirably, the blood collection needle fixation member is disposed at the inside of the insertion groove in such a manner as to perform a linear motion with respect to the blood collection needle insertion member.

Desirably, the blood collection needle fixation member includes: a conveying cam adapted to be moved along a groove formed along the upper outer periphery of the rotary shaft of the rotary member and to be linearly moved with respect to the rotating direction of the rotary member; a power transmitter adapted to transmit the linear motion of the conveying cam to the locking groove of the blood collection needle; and a fixing part adapted to fix the blood collection needle conveyed downwardly by means of the power transmitter thereto.

Desirably, the power transmitter is adapted to transmit the linear motion of the fixing cam to the blood collection needle so as to convey the blood collection needle upwardly after the blood collection operation has been finished.

Desirably, the blood collection needle ejection member is configured to be opened by moving by a given angle along a groove formed on the top cross surface of the rotary shaft of the rotary member around the fixing shaft, and includes: a protrusion adapted to be inserted into the groove formed on the top cross surface of the rotary shaft of the rotary member so as to transmit the rotary force of the rotary member; an ejection cam adapted to be rotated by a given angle by means of the rotary force of the rotary member transmitted from the protrusion; and an ejection cap disposed on the output side of the ejection cam and having a groove into which the blood collection needle is inserted formed at the inside thereof so as to escape the blood collection needle from the insertion groove by means of the rotary force of the ejection cam.

Desirably, the automated blood collection device further includes a stopper fixedly mounted along the fixing shaft so as to restrict a moving distance of the fixing part when the blood collection needle is fixed.

Desirably, the fixing cam, the guide cam, the ejection cam and the conveying cam of the automated blood collection device have the form of a cam gear.

Desirably, the fixing cam, the guide cam, the ejection cam and the conveying cam of the automated blood collection device have the form of a cam plate.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENT

Figure 1:
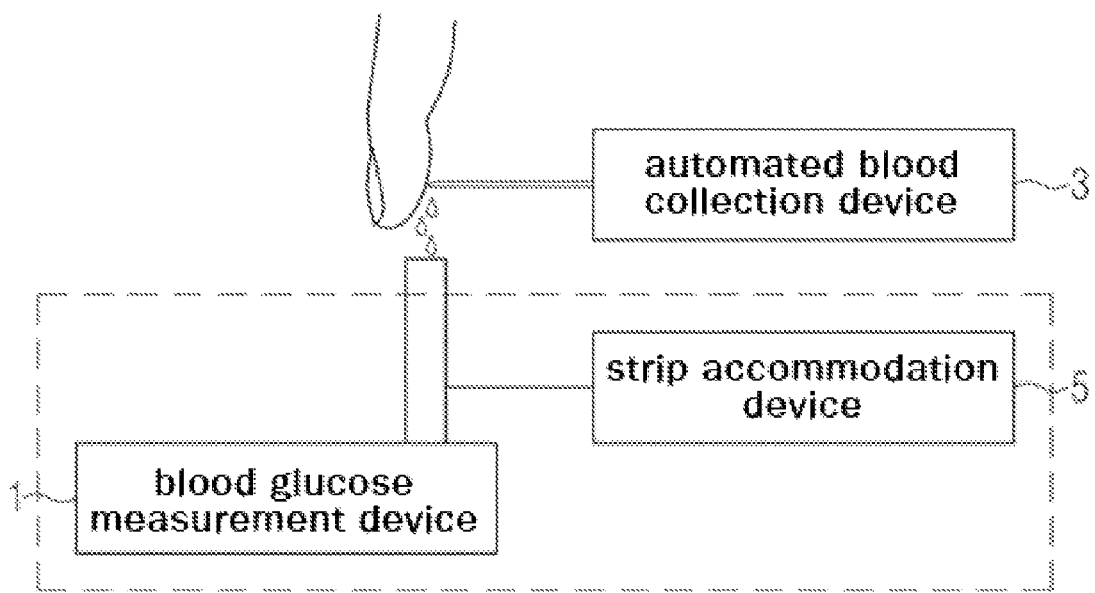
FIG. 1 is a block diagram showing a configuration of a blood glucose monitoring system according to the present invention.

So as to allow the advantages of the operations of the present invention and the objects accomplished by the preferred embodiments of the present invention to be fully understood, the preferred embodiments of the present invention should be described with reference to the attached drawings and the reference numerals denoted on the drawings.

Hereinafter, an explanation on a blood glucose monitoring system according to the present invention will be in detail given with reference to the attached drawings, wherein the same reference numerals in the drawings denote the same components as each other.

FIG. 1 is a block diagram showing a configuration of a blood glucose monitoring system according to the present invention. As shown in FIG. 1, the blood glucose monitoring system according to the present invention includes a strip accommodation device 1, an automated blood collection device 3 and a blood glucose measurement device 5.

That is, if the blood extracted from the human body through the automated blood collection device 3 is applied to a strip ejected to the outside from the strip accommodation device 1, a blood glucose level in the blood applied to the strip is displayed on the blood glucose measurement device 5.

First Embodiment of Strip Accommodation Device

Figure 2:
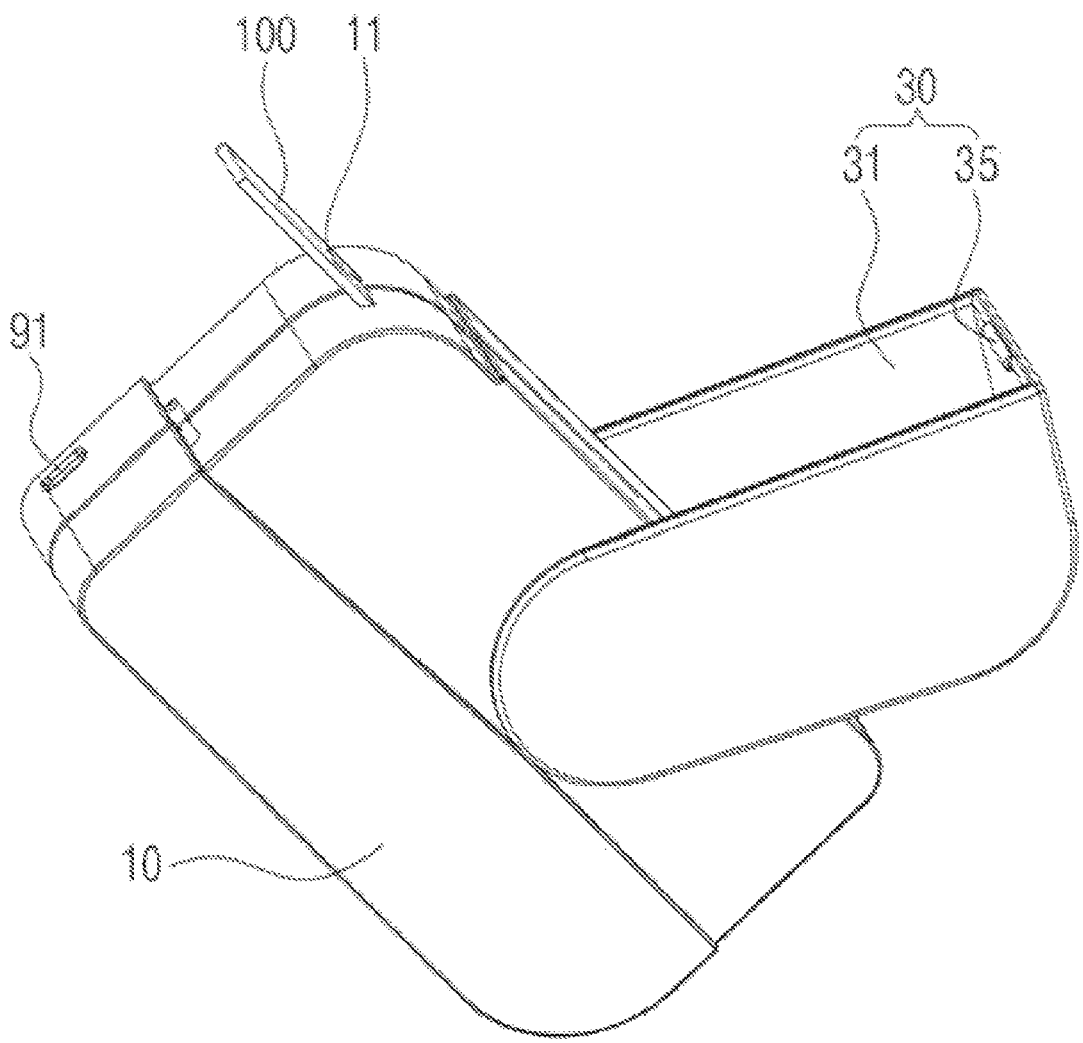
FIG. 2 is a perspective view showing a first embodiment of a strip accommodation device in the blood glucose monitoring system according to the present invention.

FIG. 2 is a perspective view showing a first embodiment of the strip accommodation device in the blood glucose monitoring system according to the present invention. As shown, the strip accommodation device 1 includes a housing 10, an operating member 30, a first conveying member 50, and a second conveying member 70.

The housing 10 has a space portion in which a plurality of strips 100 are accommodated, and the operating member 30 is opened at one side thereof to eject one of the plurality of strips 100 and adapted to be rotated to a given angle around a rotary shaft 33 mounted on the outer surface of the housing 10.

On the other hand, the housing 10 further includes a moisture remover 90 disposed at the inside thereof so as to remove moisture therefrom and a slot 91 formed at a given position thereof so as to allow the blood glucose monitoring system to be carried with the measurer. In this case, the operating member 30 is formed of a flexible material and it is molded or coated so as to maintain the airtightness with an ejection hole 11 of the strips 100 and with the slot formed on the rotary shaft 33.

Further, the operating member 30 has a cover 31 formed integrally therewith so as to seal the ejection hole 11 when rotated in the opposite direction to the ejection direction of the strip 100 after the used strip 100 has been removed.

Additionally, the operating member 30 is configured to be escaped from the housing 10 by applying a given force thereto so as to eject the strip 100 to the outside.

So as to allow the operating member 30 to be escaped from the housing 10 by the application of the given force thereto, the cover 31 has a locking projection 35 formed at the inside thereof so as to lock the cover 31 to the housing 10, and the housing 10 has a locking groove 37 formed to insert the locking projection 35 thereinto.

That is, the operating member 30 and the housing 10 are locked to each other by means of the insertion of the locking projection 35 of the cover 31 of the operating member 30 into the locking groove 37 of the housing 10.

Moreover, the rotary shaft 33 for the rotation of the operating member 30 is disposed at both outer surfaces of the housing 10.

The first conveying member 50 is disposed at the inside of the housing 10 to eject the strip 100 to the outside through the ejection hole 11 in such a manner as to convert a rotary motion of the operating member 30 into an upward linear motion and to convey the strip 100 upwardly.

That is, the first conveying member 50 has a lever 51 adapted to be rotated by the rotation of the operating member 30 and having a protrusion 51a formed thereon and a carriage 53 adapted to be conveyed upwardly by means of the movement of the protrusion 51a along a guide groove 53b through the rotation of the lever 51 and having a projection 53a adapted to forcedly eject the strip 100 positioned at an ejection hole area.

That is, the protrusion 51a of the lever 51 is formed at the opposite position to the rotary shaft 33.

In more detail, the carriage 53 has the projection 53a formed at the ejection hole area so as to eject the strip 100 positioned at the ejection hole area to the outside by the upward conveyance thereof. The projection 53a fixedly pricks one surface of the strip 100 to eject the strip 100 to the outside.

According to the present invention, the first conveying member 50 has the lever 51 and the guide groove 53b of the carriage 53 adapted to convey the carriage 53 upwardly in accordance with the rotation of the operating member 30, but it is obvious to those skilled in the art that the lever 51 and the guide groove 53b of the carriage 53 may be replaced with rack and pinion gears.

On the other hand, the second conveying member 70 has one side formed to face the ejection hole 11 of the housing 10 so as to convey the strip 100 not used yet to the ejection hole area.

That is, the second conveying member 70 has a guide 71 adapted to convey the strip 100 not used yet to empty space after the strip 100 has been ejected through the ejection hole 11 and an elastic module 73 adapted to supply a given elastic force to the guide 71 so as to allow the strip 100 not used yet to be conveyed to the ejection hole area.

According to the present invention, on the other hand, the strips 100 are accommodated in the housing 10, but the strip storage device 110 having the plurality of strips 100 accommodated therein may be detachably mounted in the housing 10 through an opening formed at a given position of the housing 10.

Figure 3:
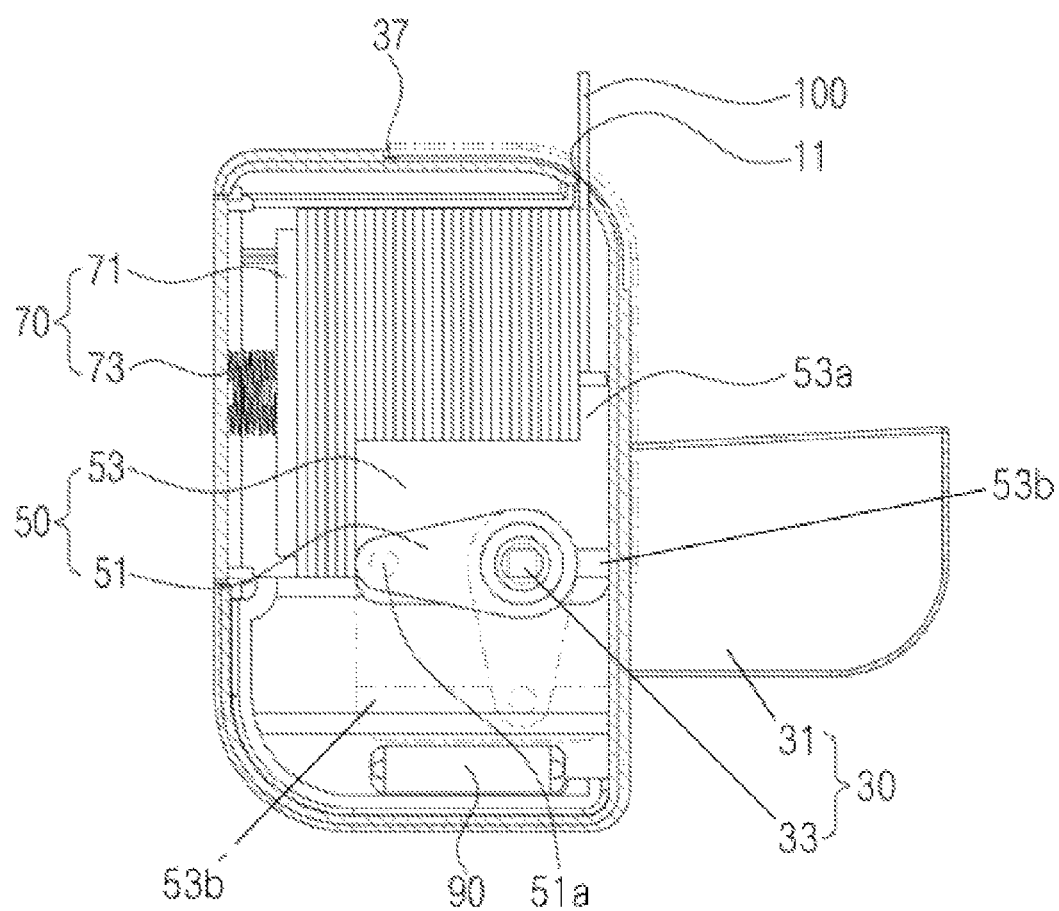
FIG. 3 is a sectional view showing a configuration of the strip accommodation device of FIG. 2.
Figure 4:
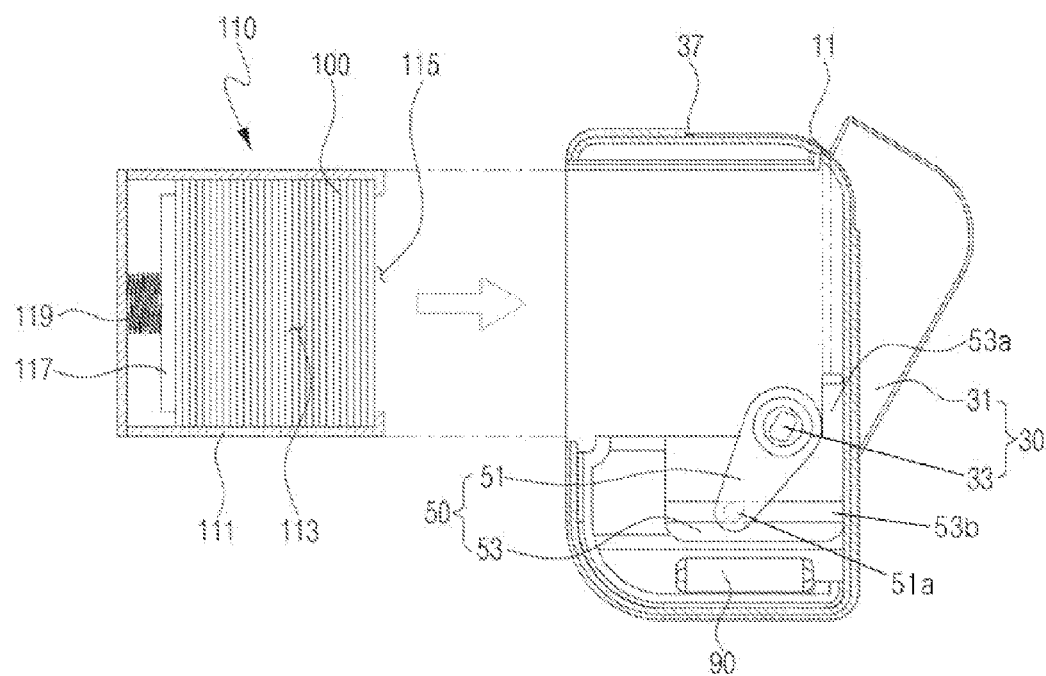
FIG. 4 is a sectional view showing a process of mounting a separate strip storage device on the strip accommodation device of FIG. 2.

FIG. 3 is a sectional view showing a configuration of the strip accommodation device of FIG. 2, and FIG. 4 is a sectional view showing a process of mounting a separate strip storage device on the strip accommodation device of FIG. 2.

That is, the strip storage device 110 has one side formed to face the ejection hole 11 of the housing 10 so as to convey the strip 100 not used yet to the ejection hole area.

The strip storage device 110 has a strip storage housing 111 having an ejection opening 115 formed on one side thereof, a strip storage member 113 formed in the strip storage housing 111 so as to store the plurality of strips 100 therein, a guide 117 adapted to convey the strip 100 not used yet to empty space in the housing 10 after the strip 100 has been ejected through the ejection opening 115 of the strip storage housing 111, and an elastic module 119 adapted to supply a given elastic force to the guide 117 so as to allow the strip 100 not used yet to be conveyed to the ejection opening area.

The housing 10 is assembled by means of ultrasound welding.

Next, an explanation on the operation of the strip accommodation device in the blood glucose monitoring system according to the present invention will be given.

As shown in FIG. 4, if a given force is applied to the operating member 30 from a measurer to cause the locking protrusion 35 of the cover 31 of the operating member 30 to be escaped from the locking groove 37 of the housing 10 and to thus cause the operating member 30 to be rotated by a given angle (for example, 180°) around the rotary shaft 33, the lever 51 is rotated together with the rotation of the operating member 30.

Next, the protrusion 51a of the lever 51 is moved along the guide groove 53b of the carriage 53 to convey the carriage 53 upwardly.

At this time, the projection 53a of the carriage 53 forcedly ejects the strip 100 positioned at the ejection hole area upwardly, such that the strip is ejected to the outside and the ejected strip 100 is inserted into the blood glucose measurement device 5 positioned on the ejection hole 11.

After that, if the operating member 30 is moved in the opposite direction to the opening direction thereof, the protrusion 51a of the lever 51 is moved downwardly along the guide groove 53b, and the locking protrusion 35 of the cover 31 of the operating member 30 is inserted into the locking groove 37 of the housing 10 by the application of a give force from the measurer thereto, thereby completely sealing the ejection hole 11.

On the other hand, the guide 71 is moved toward the ejection hole area by means of the elastic module 73 of the second conveying member 70, thereby conveying the strip 100 not used yet to the empty space of the housing 10.

If the strip storage device 110 is separately mounted, on the other hand, the strip storage device 110 is inserted into the opening of the housing 10 and the strips stored in the strip storage device 110 are conveyed to the empty space of the housing 10 through the ejection opening 115 by means of the guide 117.

After that, the strip 100 not used yet positioned in the empty space of the housing 10 is ejected to the outside through the ejection hole 11 by means of the first conveying member 50.

Second Embodiment of Strip Accommodation Device

Figure 5:
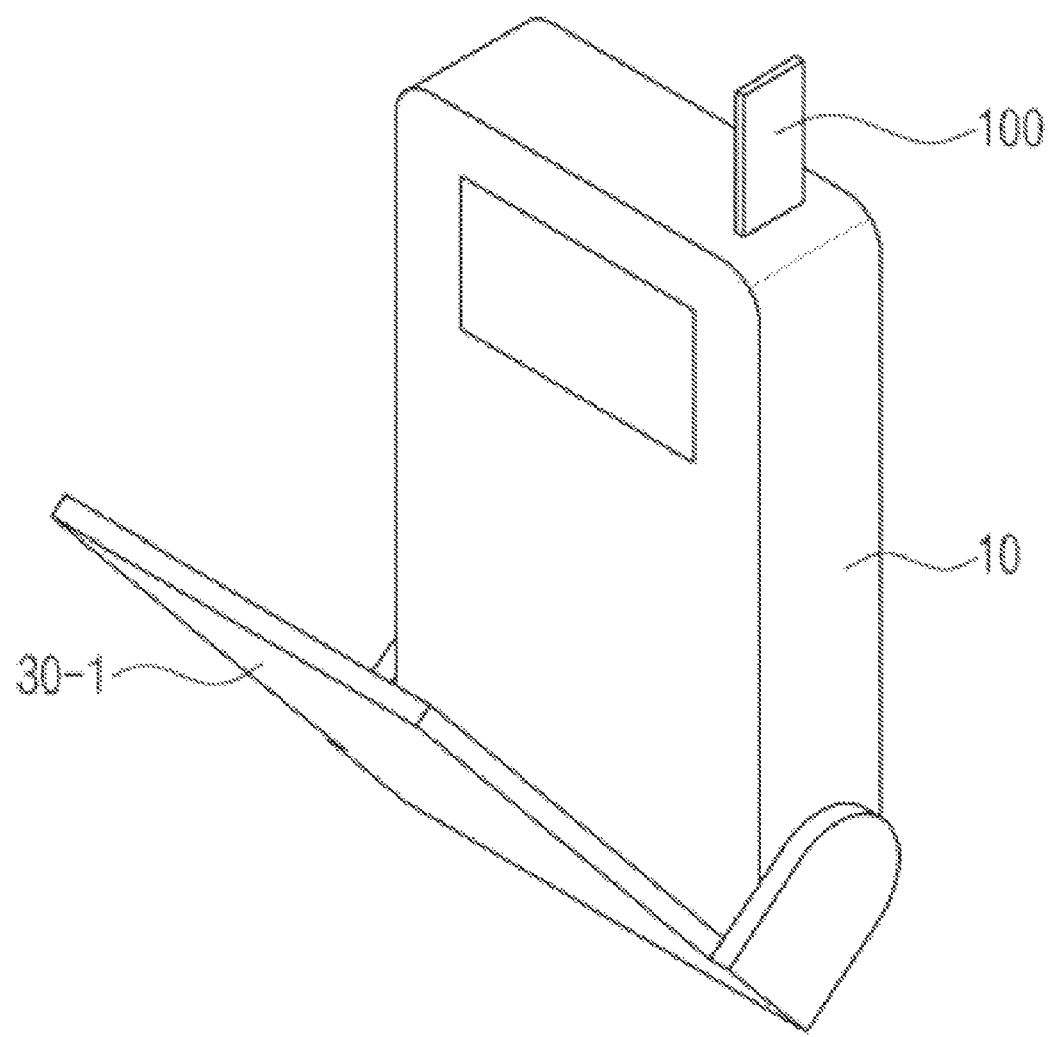
FIG. 5 is a perspective view showing a second embodiment of the strip accommodation device in the blood glucose monitoring system according to the present invention.
Figure 6:
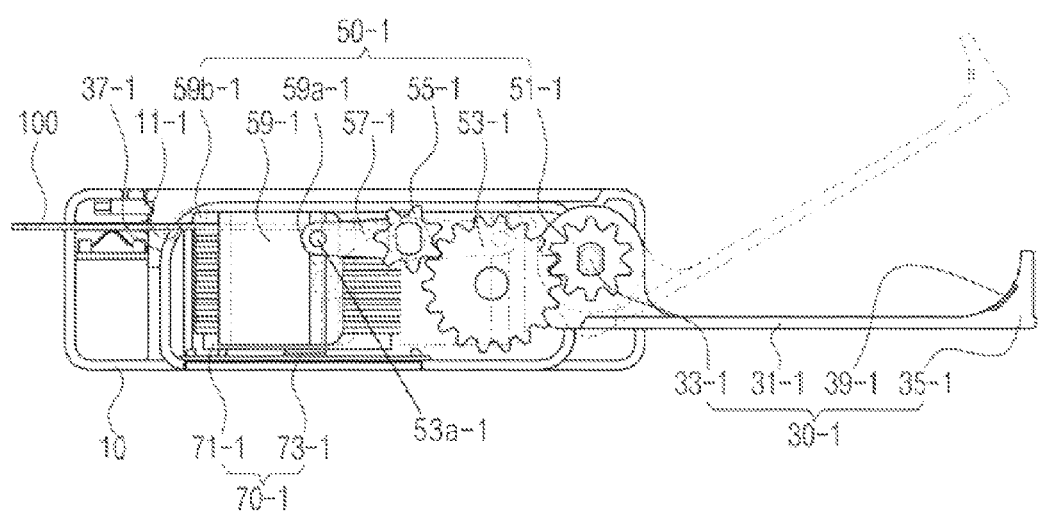
FIG. 6 is a sectional view showing an operating process of the strip accommodation device of FIG. 5.

FIG. 5 is a perspective view showing a second embodiment of the strip accommodation device in the blood glucose monitoring system according to the present invention, and FIG. 6 is a sectional view showing an operating process of the strip accommodation device of FIG. 5. As shown, the strip accommodation device 1 includes a housing 10, an operating member 30-1, a first conveying member 50-1, and a second conveying member 70-1.

The housing 10 has a space portion in which a plurality of strips 100 are accommodated, and the operating member 30-1 includes a folder type cover rotated by a first angle (150°) around a rotary shaft 33-1 disposed on the outer surfaces of the housing 10 in accordance with the opening manipulation of the measurer.

The operating member 30-1 has a cover 31-1 adapted to seal an ejection hole 11-1 when rotated in the opposite direction to the ejection direction of the strip 100 after the used strip 100 has been removed.

That is, the operating member 30-1 is configured to be escaped from the housing 10 by applying a given force thereto so as to eject the strip 100 to the outside.

So as to allow the operating member 30-1 to be escaped from the housing 10 by the application of the given force thereto, the cover 31-1 has a locking projection 35-1 formed at the inside thereof so as to lock the cover 31-1 to the housing 10, and the housing 10 has a locking groove 37-1 formed on the ejection hole area and adapted to insert the locking projection 35-1 thereinto so as to completely seal the ejection hole 11-1.

That is, the operating member 30-1 and the housing 10 are locked to each other by means of the insertion of the locking projection 35-1 of the cover 31-1 of the operating member 30-1 into the locking groove 37-1 of the housing 10 by the application of a given force thereto, thereby sealing the ejection hole 11-1.

The first conveying member 50-1 is disposed at the inside of the housing 10 and converts a rotary motion of the operating member 30-1 into an upward linear motion, thereby conveying the strip 100 upwardly.

That is, the first conveying member 50-1 has a first gear 51-1 rotated while being engaged with the rotary shaft 33-1, a second gear 53-1 rotated while being engaged with the first gear 51-1, and a third gear 55-1 rotated while being engaged with the second gear 53-1. Further, the first conveying member 50-1 includes: a lever 57-1 adapted to be coupled to the rotary shaft of the third gear 55-1 and rotated by the rotation of the third gear 55-1 and having a protrusion 53a-1 formed thereon; and a carriage 59-1 adapted to be conveyed upwardly by means of the movement of the protrusion 53a-1 along a guide groove 59a-1 through the rotation of the lever 57-1 and having a projection 59b-1 adapted to forcedly eject the strip 100 positioned at an ejection hole area.

That is, the protrusion 53a-1 of the lever 57-1 is formed at the opposite position to the rotary shaft 33-1.

In more detail, the carriage 59-1 includes the projection 59b-1 formed at the ejection hole area so as to eject the strip 100 positioned at the ejection hole area to the outside by the upward conveyance thereof.

According to the present invention, the first conveying member 50-1 has the first to third gears 51-1, 53-1 and 55-1 adapted to convey the carriage 59-1 upwardly in accordance with the rotation of the operating member 30-1, but it is obvious to those skilled in the art that the number of gears may be changed in accordance with the length of the strip, the length of the blood glucose measurement device, and the length of the lever.

On the other hand, the second conveying member 70-1 has one side formed to face the ejection hole 11-1 of the housing 10 so as to convey the strip 100 not used yet to the ejection hole area.

That is, the second conveying member 70-1 has a guide 71-1 adapted to convey the strip 100 not used yet to empty space after the strip 100 has been ejected through the ejection hole 11-1 and an elastic module 73-1 adapted to supply a given elastic force to the guide 71-1 so as to allow the strip 100 not used yet to be conveyed to the ejection hole area.

According to the present invention, on the other hand, the strips 100 are accommodated in the housing 10, but as shown in FIG. 4, the strip storage device 110 having the plurality of strips 100 accommodated therein may be detachably mounted in the housing 10 through an opening formed at a given position of the housing 10. The configuration and operation of the strip storage device 110 have been described already, and therefore, an explanation on them will be avoided for the brevity of the description.

Now, an explanation on the operation of the strip accommodation device in the blood glucose monitoring system according to the present invention will be given.

As shown in FIG. 6, if a given force is applied to the operating member 30-1 from the measurer to cause the locking protrusion 35-1 of the cover 31-1 of the operating member 30-1 to be escaped from the locking groove 37-1 of the housing 10 and to thus cause the operating member 30-1 to be rotated by the first angle around the rotary shaft 33-1 of the operating member 30-1, the first gear 51-1, the second gear 53-1 and the third gear 55-1 are sequentially rotated, and the lever 57-1 disposed on the rotary shaft of the third gear 55-1 is thus rotated.

Next, the protrusion 53a-1 of the lever 57-1 is moved along the guide groove 59a-1 of the carriage 59-1 to convey the carriage 59-1 upwardly.

At this time, the projection 59b-1 of the carriage 59-1 forcedly ejects the strip 100 positioned at the ejection hole area upwardly.

Next, if the blood collected by the blood collection needle is injected into the strip 100, the concentration of the glucose in the blood on the strip 100 is sensed and displayed by means of the blood glucose measurement device 5.

After the blood glucose measurement has been finished, if the operating member 30-1 is rotated by a second angle (180°) larger than the first angle, the protrusion 53a-1 of the lever 57-1 is moved upwardly along the guide groove 59a-1 of the carriage 59-1, such that the used strip 100 is ejected completely to the outside from the ejection hole 11-1. The process of ejecting the used strip 100 completely to the outside is the same as of ejecting the strip to the ejection hole area, and therefore, the detailed explanation will be avoided.

Next, if the operating member 30-1 is rotated in the opposite direction to the opening direction thereof, the protrusion 53a-1 of the lever 57-1 is moved downwardly along the guide groove 59a-1 of the carriage 59-1, and the locking protrusion 35-1 of the cover 31-1 of the operating member 30-1 is inserted into the locking groove 37-1 of the housing 10 by the application of a give force from the measurer thereto, thereby completely sealing the ejection hole 11-1. At this time, the cover 31-1 has a sealant 39-1 coated or molded on the portion corresponding to the area of the ejection hole 11-1 so as to seal the strips 100 stored in the housing 10.

On the other hand, the guide 71-1 is moved toward the ejection hole area by means of the elastic module 73-1 of the second conveying member 70-1, thereby conveying the strip 100 not used yet to the empty space of the housing 10.

According to the present invention, the strips 100 are mounted in the housing at the time of manufacturing the strip accommodation device, but it is obvious to those skilled in the art that a cover openable by the measurer may be further mounted at a given position of the housing where the strips are accommodated and the strip accommodation space may be sealed by means of the cover and the housing.

If the strip storage device 110 as shown in FIG. 4 is separately mounted, further, the strip storage device 110 is inserted into the opening of the housing 10, and the strips stored in the strip storage device 110 are conveyed to the empty space of the housing 10 through the ejection opening 115 by means of the guide 117.

After that, the strip 100 not used yet positioned in the empty space of the housing 10 is ejected to the outside through the ejection hole 11-1 by means of the first conveying member 50-1.

The process of ejecting the strip 100 not used yet to the outside through the ejection hole 11-1 is the same as mentioned above, and therefore, the detailed explanation will be avoided.

Third Embodiment of Strip Accommodation Device

Figure 7:
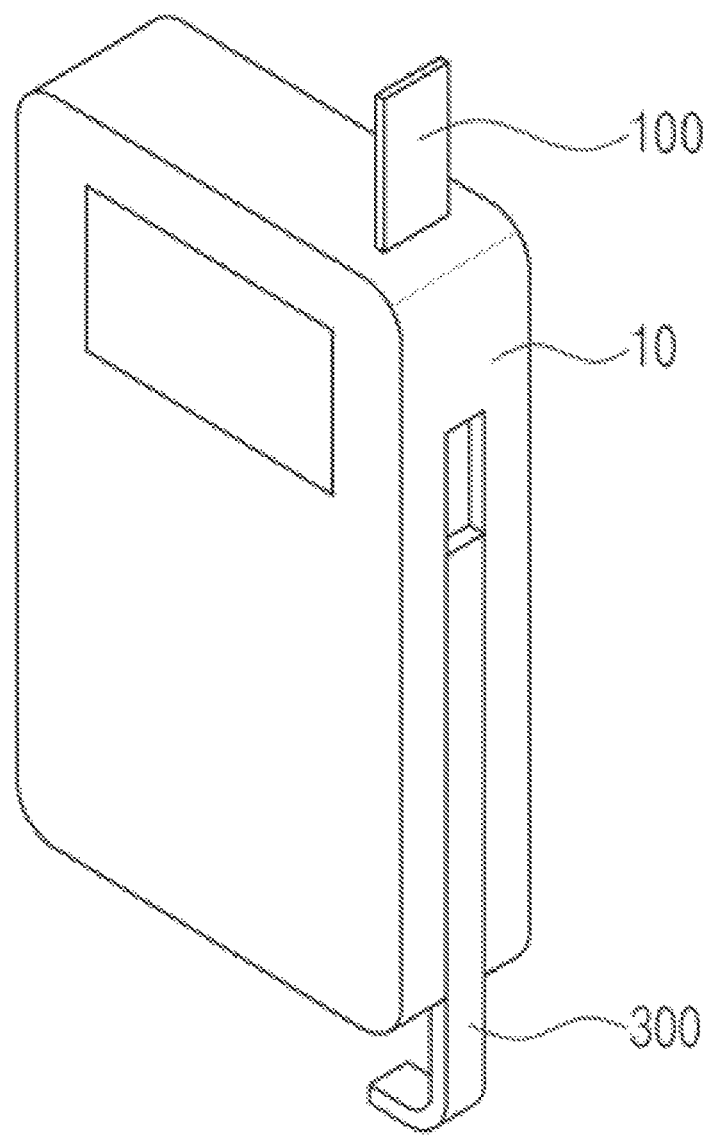
FIG. 7 is a perspective view showing a third embodiment of the strip accommodation device in the blood glucose monitoring system according to the present invention.
Figure 8:
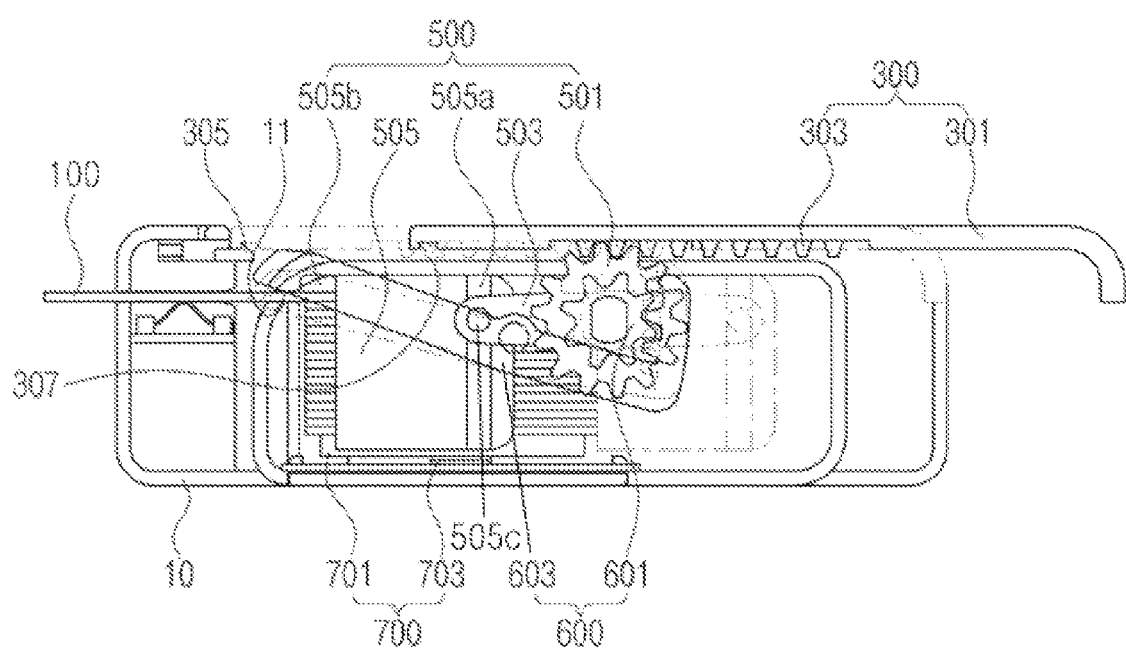
FIG. 8 is a sectional view showing a configuration of the strip accommodation device in the blood glucose monitoring system according to the present invention.

FIG. 7 is a perspective view showing a third embodiment of the strip accommodation device in the blood glucose monitoring system according to the present invention, and FIG. 8 is a sectional view showing a configuration of the strip accommodation device in the blood glucose monitoring system according to the present invention.

According to the third embodiment, as shown, the strip accommodation device includes a housing 10 of the blood glucose measurement device, an operating member 300, a first conveying member 500, a sealing member 600, and a second conveying member 700.

The housing 10 has a space portion in which a plurality of strips 100 is accommodated, and the operating member 300 includes a slide type cover 301. In more detail, the operating member 300 has a rack gear 303 disposed at a given position on the inner surface of the cover 301.

The rack gear 303, which is disposed at a given position on the inner surface of the cover 301, is activated as a motor being rotated by the operation of the cover 301, which is very obvious to those skilled in the art. Thus, the detailed description of the rack gear 303 is avoided.

That is, the operating member 300 is configured to be escaped from the housing 10 by applying a given force thereto so as to eject the strip 100 to the outside.

So as to allow the operating member 300 to be escaped from the housing 10 by the application of the given force thereto, the cover 301 has a locking projection 307 formed at the inside thereof so as to lock the cover 301 to the housing 10, and the housing 10 has a locking groove 305 formed on the area around an ejection hole 11 and adapted to insert the locking projection 307 thereinto so as to completely seal the ejection hole 11.

That is, the operating member 300 and the housing 10 are locked to each other by means of the insertion of the locking projection 307 of the cover 301 of the operating member 300 into the locking groove 305 of the housing 10 by the application of a given force thereto.

The first conveying member 500 has a pinion gear 501 disposed at the inside of the housing 10 in such a manner as to be engaged with the rack gear 303 to convert a downward linear motion of the operating member 300 into a rotary motion, thereby ejecting the strip 100 to the outside through the ejection hole 11.

That is, the first conveying member 500 has the pinion gear 501 adapted to convert the linear motion of the rack gear 303 of the operating member 300 into a rotary motion, a lever 503 disposed on the rotary shaft of the pinion gear 501 in such a manner as to be rotated by the rotation of the pinion gear 501 and having a protrusion formed at the opposite position to the rotary shaft of the pinion gear 501, and a carriage 505 adapted to be conveyed upwardly by means of the movement of the protrusion along a guide groove 505a through the rotation of the lever 503 and having a projection 505b adapted to forcedly eject the strip 100 positioned at the ejection hole area.

In more detail, the carriage 505 further includes the projection 505b formed at the ejection hole area so as to eject the strip 100 positioned at the ejection hole area to the outside by the upward conveyance thereof.

After the blood glucose measurement has been finished, if the operating member 300 is linearly moved more downwardly than the linear moving position thereof so as to eject the strip 100 through the ejection hole 11, the first conveying member 500 ejects the used strip 100 positioned on the ejection hole 11 to the outside.

The sealing member 600 includes a cam gear 601 coupled on the rotary shaft of the pinion gear 501 in such a manner as to be rotated together with the pinion gear 501 rotated by the linear motion of the rack gear 303 of the operating member 300 and a sealing lever 603 coupled on the rotary shaft of the cam gear 601 in such a manner as to moved by a given angle in accordance with the rotation of the cam gear 601 and to completely seal the ejection hole 11 after the used strip 100 has been ejected to the outside.

On the other hand, the second conveying member 700 has one side formed to face the ejection hole 11 of the housing 10 so as to convey the strip 100 not used yet to the ejection hole area.

That is, the second conveying member 700 has a guide 701 adapted to convey the strip 100 not used yet to empty space after the strip 100 has been ejected through the ejection hole 11 and an elastic module 703 adapted to supply a given elastic force to the guide 701 so as to allow the strip 100 not used yet to be conveyed to the ejection hole area.

According to the present invention, on the other hand, the strips 100 are accommodated in the housing 10, but as shown in FIG. 4, the strip storage device 110 having the plurality of strips 100 accommodated therein may be detachably mounted in the housing 10 through an opening formed at a given position of the housing 10. The configuration and operation of the strip storage device 110 have been described already, and therefore, an explanation on them will be avoided for the brevity of the description.

After that, the housing 10 is assembled by means of ultrasound welding.

Now, an explanation on the operation of the strip accommodation device according to the present invention will be given.

As shown in FIG. 8, if a given force is applied to the cover 301 of the operating member 300 from the measurer to cause the operating member 300 to be moved downwardly, the rack gear 303 disposed at the inside of the cover 301 is linearly moved downwardly.

Through the downward linear motion of the rack gear 303, the pinion gear 501 of the first conveying member 500 being engaged with the rack gear 303 is rotated, and as a result, the lever 503 is rotated.

At the same time, the cam gear 601 of the sealing member 600 is rotated, such that the sealing lever 603 is moved by a given angle. The movement of the sealing lever 603 permits the ejection hole 11 to be opened.

Therefore, the protrusion 505c of the lever 503 is moved along the guide groove 505a of the carriage 505, thereby conveying the carriage 505 upwardly.

At this time, the projection 505b of the carriage 505 forcedly ejects the strip 100 positioned at the ejection hole area upwardly through the ejection hole 11 opened by means of the sealing lever 603.

Next, if the blood collected by the blood collection needle is injected into the strip 100, the concentration of the glucose in the blood on the strip 100 is sensed and displayed by means of the blood glucose measurement device 5.

After the blood glucose measurement has been finished, if the cover 301 of the operating member 300 is linearly moved more downwardly than the position of the cover 301 for the blood glucose measurement, the protrusion 505c of the lever 503 is moved more upwardly along the guide groove 505a of the carriage 505, such that the used strip 100 is ejected completely to the outside from the ejection hole 11-1. The process of ejecting the used strip 100 completely to the outside is the same as of ejecting the strip to the ejection hole area, and therefore, the detailed explanation will be avoided.

Next, if the cover 301 of the operating member 300 is linearly moved upwardly in the opposite direction to the downward linear movement thereof, the rack gear 303 is linearly moved upwardly, and thus, the lever 503 is moved downwardly along the guide groove 505a of the carriage 505 in accordance with the rotation of the pinion gear 501 being engaged with the rack gear 303.

As the pinion gear 501 is rotated, at this time, the cam gear 601 of the sealing member 600 is rotated to move the sealing lever 603 by a given angle, thereby completely sealing the ejection hole 11.

On the other hand, the guide 701 is moved toward the ejection hole area by means of the elastic module 703 of the second conveying member 700, thereby conveying the strip 100 not used yet to the empty space of the housing 10.

According to the present invention, the strips 100 are mounted in the housing at the time of manufacturing the strip accommodation device, but it is obvious to those skilled in the art that a cover openable by the measurer may be further mounted at a given position of the housing where the strips are accommodated and the strip accommodation space may be sealed by means of the cover and the housing.

Embodiment of Automated Blood Collection Device

Figure 9:
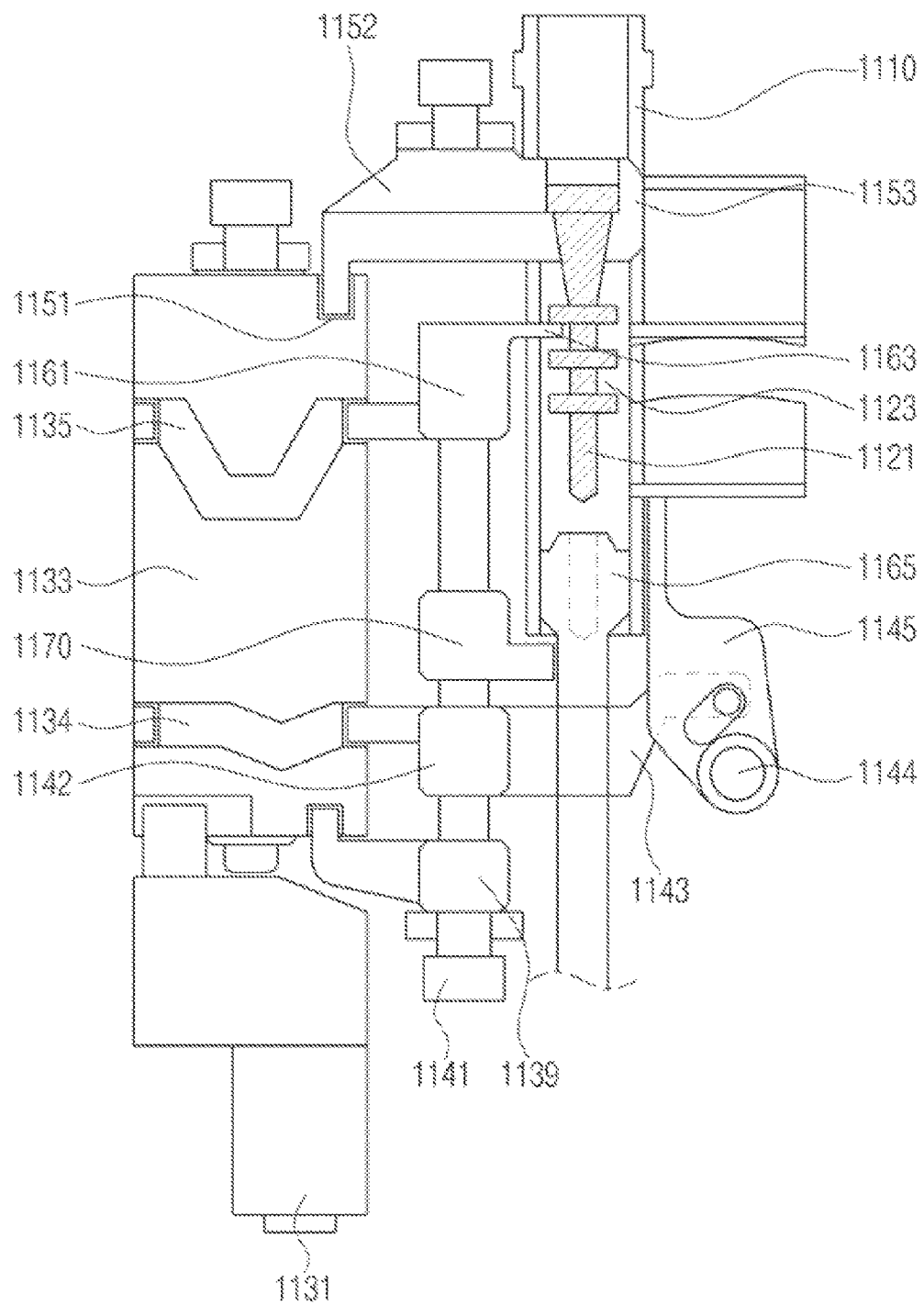
FIG. 9 is a sectional view showing a configuration of an automated blood collection device in the blood glucose monitoring system according to the present invention.
Figure 10:
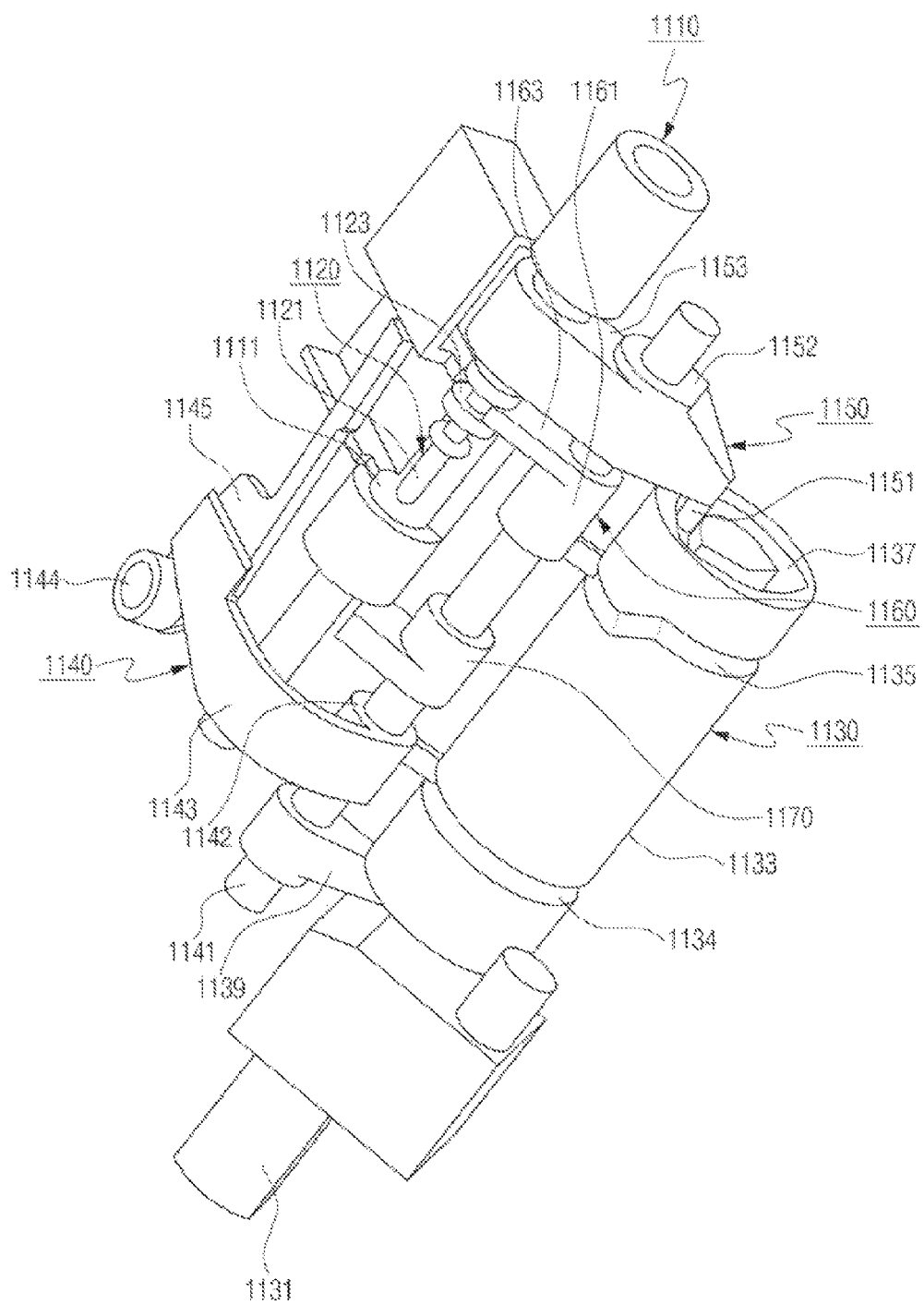
FIG. 10 is a bottom view showing the automated blood collection device of FIG. 9.
Figure 11:
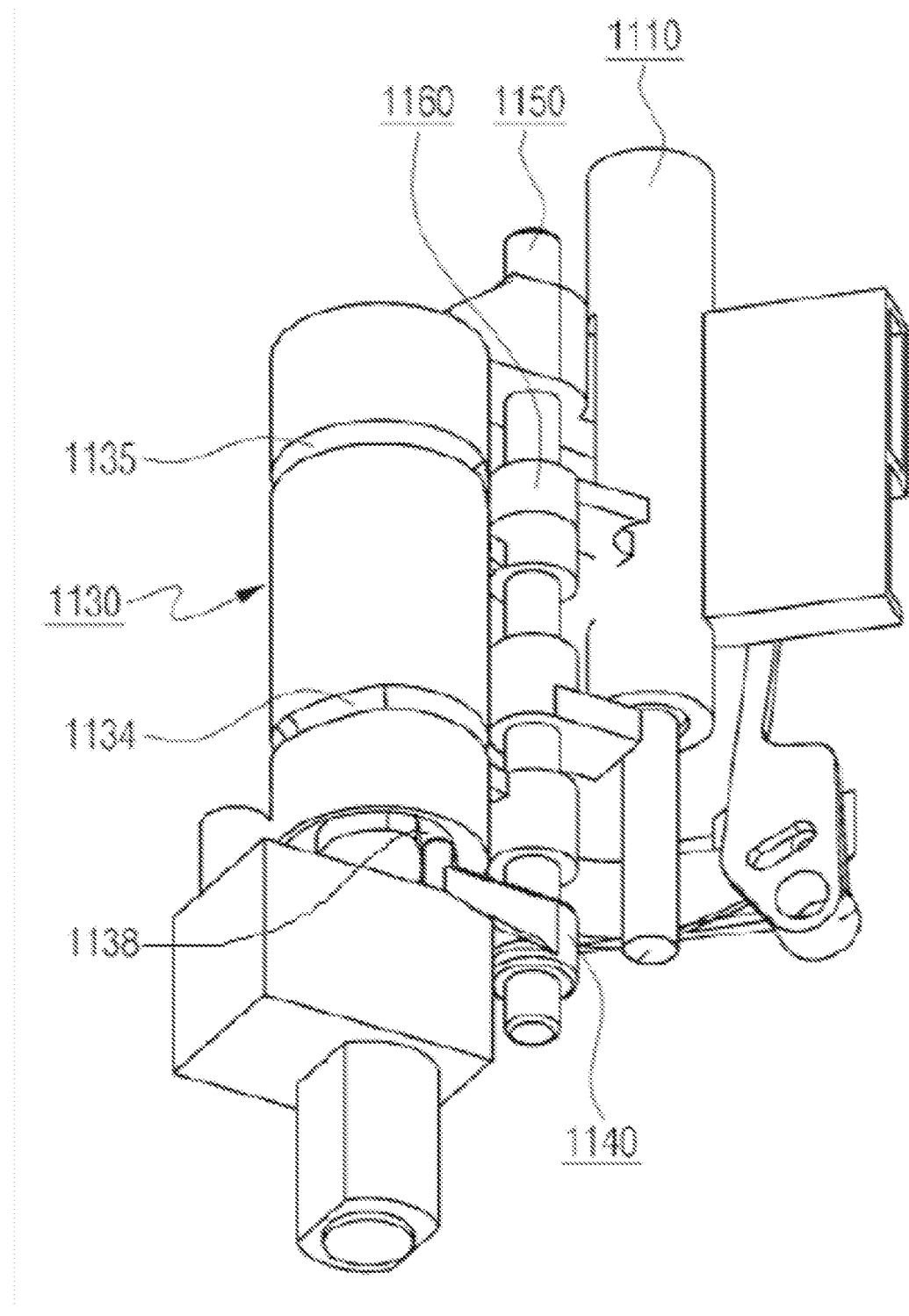
FIG. 11 is a perspective view showing the automated blood collection device of FIG. 9.

FIG. 9 is a sectional view showing a configuration of an automated blood collection device in the blood glucose monitoring system according to the present invention, FIG. 10 is a bottom view showing the automated blood collection device of FIG. 9, and FIG. 11 is a perspective view showing the automated blood collection device of FIG. 9.

According to the present invention, as shown in FIGS. 9 to 11, the automated blood collection device in the blood glucose monitoring system is configured wherein as the rotary force of a motor is received, a blood collection needle is guided and inserted into an insertion groove and is automatically moved downwardly to perform blood collection, and after that, the blood collection needle used for the blood collection is ejected to the outside. The automated blood collection device largely includes a blood collection needle insertion member 1110, a blood collection needle 1120, a rotary member 1130, a blood collection needle guide member 1140, a blood collection needle ejection member 1150, and a blood collection needle fixation member 1160.

In this case, the blood collection needle insertion member 1110 has an insertion groove 1111 having an opened semicircular portion and adapted to insert the blood collection needle 1120 thereinto.

Also, the blood collection needle 1120 is guided and fixed to the insertion groove 1111 by means of the blood collection needle guide member 1140.

That is, the blood collection needle 1120 includes: a conveying shaft 1121 having one side inserted into a groove formed on the blood collection needle ejection member 1150 and the other side conveyed downwardly to fix the blood collection needle 1120 by means of the blood collection needle fixation member 1160; and a locking groove 1123 fixedly formed at a given position of the conveying shaft 1121 in such a manner as to be lockedly coupled to the blood collection needle fixation member 1160.

On the other hand, the rotary member 1130 is typically rotated by receiving the rotary force from a motor 1131 and includes a rotary shaft 1133 having grooves 1134 and 1135 of given shapes formed along the outer periphery thereof and other grooves 1137 and 1138 of given shapes formed on the top and underside cross sections thereof.

Also, the rotary member 1130 further includes a fixing cam 1139 adapted to be moved along the groove 1138 formed on the underside cross section thereof so as to fix a fixing shaft 1141 as will be discussed later thereto.

The blood collection needle guide member 1140 is adapted to convert a rotary motion of the rotary member 1130 into upward and downward motions around the fixing shaft 1141 and thus convert the converted upward and downward motions into left and right motions, thereby guiding the blood collection needle 1120 to the insertion groove 1111.

That is, the blood collection needle guide member 1140 includes: a guide cam 1142 adapted to be moved along the groove 1134 formed along the rotary shaft 1133 of the rotary member 1130 in such a manner as to perform the upward and downward motions around the fixing shaft 1141; a guide transmitter 1143 disposed on the other side of the guide cam 1142 so as to transmit the upward and downward motions of the guide cam 1142; and a guide lever 1145 adapted to convert the upward and downward motions of the guide cam 1142 received from the guide transmitter 1143 into the left and right motions around a rotary shaft 1144 so as to guide the blood collection needle 1120 to the insertion groove 1111.

The guide lever 1145 to which the upward and downward motions are received from the guide transmitter 1143 is insertedly fitted to an elongated hole, and as the guide lever 1145 is moved, the upward and downward motions of the guide cam 1142 are converted into the left and right motions.

Also, the blood collection needle fixation member 1160 is adapted to convert the rotary force of the rotary member 1130 into upward and downward motions and to convey the blood collection needle 1120 downwardly, such that the underside cross section of the conveying shaft 1121 of the blood collection needle 1120 can be fixed to a fixing part 1165.

In this case, the blood collection needle fixation member 1160 includes: a conveying cam 1161 adapted to be moved along the groove 1135 formed along the rotary shaft 1133 of the rotary member 1130 and to be linearly moved with respect to the rotating direction of the rotary member 1130; a power transmitter 1163 adapted to receive the linear motion of the conveying cam 1161 and to transmit the linear motion to the locking groove 1123 of the blood collection needle 1120, and the fixing part 1165 adapted to insert the conveying shaft 1121 of the blood collection needle 1120 thereinto and to fix the blood collection needle 1120 thereto at the time when the blood collection needle 1120 is moved downwardly by means of the power transmitter 1163.

When the blood collection needle 1120 is moved downwardly by means of the power transmitter 1163, the blood collection needle 1120 is fixed by the fixing part 1165, and after that, when the blood collection needle 1120 is moved upwardly by means of the conveying cam 1161, the blood collection needle 1120 is escaped from the fixing part 1165 and is moved to the blood collection needle ejection member 1150.

Further, the automated blood collection device further includes a stopper 1170 fixedly mounted along the fixing shaft 1141 and adapted to restrict a moving distance of the fixing part 1165 when the conveying shaft 1121 is downwardly fixed thereto by means of the blood collection needle fixation member 1160.

On the other hand, the blood collection needle ejection member 1150 is adapted to be rotated by a given angle around the fixing shaft 1141 by receiving the rotary motion of the rotary member 1130 to allow the blood collection needle 1120 used for the blood collection to be escaped from the insertion groove 1111.

That is, the blood collection needle ejection member 1150 is configured to be opened by moving by a given angle along the groove 1137 formed on the top cross surface of the rotary shaft 1133 of the rotary member 1130 around the fixing shaft 1141.

The blood collection needle ejection member 1150 includes: a protrusion 1151 adapted to be inserted into the groove 1137 so as to transmit the rotary force of the rotary member 1130; an ejection cam 1152 adapted to be rotated by a given angle by means of the rotary force of the rotary member 1130 transmitted from the protrusion 1151; and an ejection cap 1153 disposed on the output side of the ejection cam 1152 and having a groove into which the blood collection needle 1120 is inserted formed at the inside thereof so as to escape the blood collection needle 1120 from the insertion groove 1111 by means of the rotary force of the ejection cam 1152.

According to the present invention, the fixing cam 1139, the guide cam 1142, the ejection cam 1152 and the conveying cam 1161 have the form of a cam gear, but they may have the form of a cam plate, which is obvious to those skilled in the art. Therefore, the detailed explanation of them will be avoided.

Under the above-mentioned configuration, first, the rotary force of the motor 1131 of the rotary member 1130 is transmitted to the rotary shaft 1133, thereby rotating the rotary shaft 1133.

At this time, the guide cam 1142 of the blood collection needle guide member 1140 is moved along the groove 1134 of the rotary shaft 1133 to convert the rotary motion into the upward and downward motions, thereby transmitting the upward and downward motions to the guide lever 1145 through the guide transmitter 1143.

At this time, the upward and downward motions are converted into the left and right motions by means of the rotary shaft 1144, and the conversion into the left and right motions enables the guide lever 1145 to be moved in left and right directions.

After that, the blood collection needle 1120 stored in a blood collection needle storing case (not shown) is guided to the insertion groove 1111 of the blood collection needle insertion member 1110 by means of the guide lever 1145.

Next, since the conveying cam 1161 of the blood collection needle fixation member 1160 is moved along the groove 1135 of the rotary shaft 1133, the rotary motion of the rotary member 1130 is converted into the downward motion.

As a result, the downward motion converted by means of the conveying cam 1161 is transmitted to the locking groove 1123 by means of the power transmitter 1163, and the transmitted downward motion enables the conveying shaft 1121 of the blood collection needle 1120 to be moved downwardly.

At this time, the conveying shaft 1121 of the blood collection needle 1120 is fixedly inserted into the fixing part 1165.

After that, the blood collection needle 1120 is injected by means of a separate injection device and performs the blood collection. The configuration and operation of the injection device have been well known to those skilled in the art, and therefore, the detailed explanation of them will be avoided.

After the blood collection has been finished, next, the conveying cam 1161 of the blood collection needle fixation member 1160 is moved along the groove 1135 of the rotary shaft 1133, thereby converting the rotary motion of the rotary member 1130 into the upward motion.

The upward motion of the conveying cam 1161 is transmitted to the locking groove 1123 of the blood collection needle 1120 and moves the conveying shaft 1121 of the blood collection needle 1120 upwardly.

That is, the conveying shaft 1121 of the blood collection needle 1120 is moved upwardly to cause the blood collection needle 1120 used for the blood collection to be conveyed upwardly.

Also, the protrusion 1151 of the blood collection needle ejection member 1150 is moved along the groove 1137 formed on the top cross section of the rotary shaft 1133, such that the ejection cam 1152 is rotated by a given angle determined by means of the groove 1137.

The rotation of the ejection cam 1152 by the given angle is transmitted to the ejection cap 1153, and as a result, the ejection cap 1153 is rotated to the given angle. The rotation of the ejection cap 1153 enables the blood collection needle 1120 to be escaped from the insertion groove 1111.

That is, the blood collection needle 1120 used for the blood collection is completely ejected to the outside.

As described above, according to the present invention, the blood collection needle is guided by means of the blood collection needle guide member and is then inserted into the insertion groove, and the inserted blood collection needle is moved downwardly and fixed by means of the blood collection needle fixation member. After the blood collection, next, the blood collection needle is escaped from the insertion groove by means of the blood collection needle ejection member rotated by the given angle and is then ejected to the outside. Therefore, all of the processes of inserting and ejecting the blood collection needle are automatically carried out, thereby performing the blood collection in easier and more convenient manners.

Moreover, according to the present invention, the rotary motion of the operating member mounted on the outer surface of the housing is converted into the upward linear motion and one of the plurality of strips is automatically ejected through the ejection hole, such that the blood glucose monitoring system can be easily carried with the measurer and manipulated by him, and additionally, the strips are mounted on the blood glucose monitoring system, without any additional manipulation of the measurer, such that errors on measured data caused by the moisture, contamination or foreign matters on the strips can be previously prevented.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A blood glucose monitoring system comprising:
an automated blood collection device;
a strip accommodation device formed integrally with a blood glucose measurement device so as to convert a rotary motion of an operating member into an upward linear motion of a carriage and to automatically eject one of a plurality of strips through an ejection hole formed thereon; and
the blood glucose measurement device adapted to measure the concentration of glucose in the collected blood by means of the strip ejected from the strip accommodation device,
wherein the strip accommodation device comprises a housing adapted to contain the plurality of strips arranged serially to collect blood thereon, the operating member disposed on an outer surface of the housing in such a manner as to be opened at one side thereof to insert the housing into the inside thereof and adapted to be rotated by a given angle around a rotary shaft disposed on the outer surface of the housing, and a first conveying member disposed on a given position in the housing and adapted to convert the rotary motion of the operating member into the upward linear motion of the carriage so as to eject the strip through the ejection hold to the outside;
the strip accommodation device further comprises a second conveying member disposed on a given position in the housing in such a manner as to have one side opposite to the ejection hole formed on the housing so as to convey the strip not used yet to the ejection hole area;
the operating member has a cover formed integrally therewith so as to seal the ejection hole when rotated in the opposite direction to the ejection direction of the strip after the used strip has been removed; and
the first conveying member comprises: a lever rotated by the rotation of the operating member and having a protrusion formed at the opposite position to the rotary shaft of the operating member, wherein the carriage is adapted to be conveyed upwardly by the movement of the protrusion of the lever along a guide groove through the rotation of the lever and having a projection adapted to forcedly eject the strip positioned at the ejection hole area.

2. The blood glucose monitoring system according to claim 1, wherein the first conveying member further comprises: a gear module adapted to convert the rotary motion of the operating member into the upward linear motion, wherein the carriage is adapted to be moved upwardly by the gear module so as to eject the strip through the ejection hole.

3. The blood glucose monitoring system according to claim 1, wherein the second conveying member comprises: a guide adapted to convey the strip not used yet to empty space after the strip has been ejected through the ejection hole; and an elastic module adapted to supply a given elastic force to the guide so as to allow the strip not used yet to be conveyed to the ejection hole area.

4. The blood glucose monitoring system according to claim 3, wherein the housing further comprises a moisture remover disposed at a given position therein so as to remove moisture therefrom.

5. The blood glucose monitoring system according to claim 4, wherein the cover of the operating member has a locking projection formed at the inside thereof so as to lock the cover to the housing, and the housing has a locking groove formed to insert the locking projection of the cover thereinto.

6. The blood glucose monitoring system according to claim 5, wherein the housing has a slot formed at a given position thereof so as to allow the blood glucose monitoring system to be carried along the measurer.

7. A blood glucose monitoring system comprising:
an automated blood collection device;
a strip accommodation device formed integrally with a blood glucose measurement device so as to convert a rotary motion of an operating member into an upward linear motion of a carriage and to automatically eject one of a plurality of strips through an ejection hole formed thereon; and the blood glucose measurement device adapted to measure the concentration of glucose in the collected blood by means of the strip ejected from the strip accommodation device, wherein the automated blood collection device comprises:

a blood collection needle insertion member having an insertion groove having an opened semicircular portion and adapted to insert a blood collection needle thereinto;

a rotary member adapted to be rotated by receiving a rotary force from a motor;

a blood collection needle guide member adapted to convert a rotary motion of the rotary member into upward and downward motions around a fixing shaft and to thus convert the converted upward and downward motions into left and right motions so as to guide the blood collection needle to the insertion groove;

a blood collection needle fixation member adapted to convert the rotary force of the rotary member into upward and downward motions so as to convey the blood collection needle downwardly and fix the blood collection needle thereto and to convey the blood collection needle upwardly after blood collection has been finished; and a blood collection needle ejection member adapted to be rotated by a given angle around the fixing shaft by receiving the rotary motion of the rotary member so as to allow the blood collection needle used for the blood collection to be escaped from the insertion groove.

8. The blood glucose monitoring system according to claim 7, wherein the automated blood collection device further comprises a fixing cam adapted to be moved along a groove formed on the underside cross section of the rotary member so as to fix the fixing shaft to the rotary member.

9. The blood glucose monitoring system according to claim 8, wherein the blood collection needle guide member comprises: a guide cam adapted to be moved along a groove formed along the lower outer periphery of a rotary shaft of the rotary member at a first side of the guide cam in such a manner as to perform upward and downward motions of the guide cam around the fixing shaft; a guide transmitter disposed on a second side of the guide cam so as to transmit the upward and downward motions of the guide cam; and a guide lever adapted to convert the upward and downward motions of the guide cam received from the guide transmitter into left and right motions around a transmitting rotary shaft thereof so as to guide the blood collection needle to the insertion groove.

10. The blood glucose monitoring system according to claim 9, wherein the blood collection needle comprises: a conveying shaft having one side inserted into a groove formed on the blood collection needle ejection member and the other side conveyed downwardly to fix the blood collection needle by the blood collection needle fixation member; and a locking groove fixedly formed at a given position of the conveying shaft in such a manner as to be lockedly coupled to the blood collection needle fixation member.

11. The blood glucose monitoring system according to claim 10, wherein the blood collection needle fixation member is disposed at the inside of the insertion groove in such a manner as to perform a linear motion with respect to the blood collection needle insertion member.

12. The blood glucose monitoring system according to claim 11, wherein the blood collection needle fixation member comprises: a conveying cam adapted to be moved along a groove formed along the upper outer periphery of the rotary shaft of the rotary member and to be linearly moved with respect to the rotating direction of the rotary member; a power transmitter adapted to transmit the linear motion of the conveying cam to the locking groove of the blood collection needle; and a fixing part adapted to fix the blood collection needle conveyed downwardly by the power transmitter thereto.

13. The blood glucose monitoring system according to claim 12, wherein the power transmitter is adapted to transmit the linear motion of the fixing cam to the blood collection needle so as to convey the blood collection needle upwardly after the blood collection operation has been finished.

14. The blood glucose monitoring system according to claim 13, wherein the blood collection needle ejection member is configured to be opened by moving by a given angle along a groove formed on the top cross surface of the rotary shaft of the rotary member around the fixing shaft, and comprises: a protrusion adapted to be inserted into the groove formed on the top cross surface of the rotary shaft of the rotary member so as to transmit the rotary force of the rotary member; an ejection cam adapted to be rotated by a given angle by of the rotary force of the rotary member transmitted from the protrusion; and an ejection cap disposed on the output side of the ejection cam and having a groove into which the blood collection needle is inserted formed at the inside thereof so as to escape the blood collection needle from the insertion groove by the rotary force of the ejection cam.

15. The blood glucose monitoring system according to claim 14, wherein the automated blood collection device further comprises a stopper fixedly mounted along the fixing shaft so as to restrict a moving distance of the fixing part when the blood collection needle is fixed.

16. The blood glucose monitoring system according to claim 15, wherein the fixing cam, the guide cam, the ejection cam and the conveying cam of the automated blood collection device have the form of a cam gear.

17. The blood glucose monitoring system according to claim 16, wherein the fixing cam, the guide cam, the ejection cam and the conveying cam of the automated blood collection device have the form of a cam plate.

18. An automated blood collection device comprising: a blood collection needle insertion member having an insertion groove having an opened semicircular portion and adapted to insert a blood collection needle thereinto; a rotary member adapted to be rotated by receiving a rotary force from a motor; a blood collection needle guide member adapted to convert a rotary motion of the rotary member into upward and downward motions around a fixing shaft and to thus convert the converted upward and downward motions into left and right motions so as to guide the blood collection needle to the insertion groove; a blood collection needle fixation member adapted to convert the rotary force of the rotary member into upward and downward motions so as to convey the blood collection needle downwardly and fix the blood collection needle thereto and to convey the blood collection needle upwardly after blood collection has been finished; and a blood collection needle ejection member adapted to be rotated by a given angle around the fixing shaft by receiving the rotary motion of the rotary member so as to allow the blood collection needle used for the blood collection to be escaped from the insertion groove.

19. The automated blood collection device according to claim 18, further comprising a fixing cam adapted to be moved along a groove formed on the underside cross section of the rotary member so as to fix the fixing shaft to the rotary member.

20. The automated blood collection device according to claim 19, wherein the blood collection needle guide member comprises: a guide cam adapted to be moved along a groove formed along the lower outer periphery of a rotary shaft of the rotary member at a first side of the guide cam in such a manner as to perform upward and downward motions of the guide cam around the fixing shaft; a guide transmitter disposed on a second side of the guide cam so as to transmit the upward and downward motions of the guide cam; and a guide lever adapted to convert the upward and downward motions of the guide cam received from the guide transmitter into left and right motions around a transmitting rotary shaft thereof so as to guide the blood collection needle to the insertion groove.

21. The automated blood collection device according to claim 20, wherein the blood collection needle comprises: a conveying shaft having one side inserted into a groove formed on the blood collection needle ejection member and the other side conveyed downwardly to fix the blood collection needle by the blood collection needle fixation member; and a locking groove fixedly formed at a given position of the conveying shaft in such a manner as to be lockedly coupled to the blood collection needle fixation member.

22. The automated blood collection device according to claim 21, wherein the blood collection needle fixation member is disposed at the inside of the insertion groove in such a manner as to perform a linear motion with respect to the blood collection needle insertion member.

23. The automated blood collection device according to claim 22, wherein the blood collection needle fixation member comprises: a conveying cam adapted to be moved along a groove formed along the upper outer periphery of the rotary shaft of the rotary member and to be linearly moved with respect to the rotating direction of the rotary member; a power transmitter adapted to transmit the linear motion of the conveying cam to the locking groove of the blood collection needle; and a fixing part adapted to fix the blood collection needle conveyed downwardly by the power transmitter thereto.

24. The automated blood collection device according to claim 23, wherein the power transmitter is adapted to transmit the linear motion of the fixing cam to the blood collection needle so as to convey the blood collection needle upwardly after the blood collection operation has been finished.

25. The automated blood collection device according to claim 24, wherein the blood collection needle ejection member is configured to be opened by moving by a given angle along a groove formed on the top cross surface of the rotary shaft of the rotary member around the fixing shaft, and comprises: a protrusion adapted to be inserted into the groove formed on the top cross surface of the rotary shaft of the rotary member so as to transmit the rotary force of the rotary member; an ejection cam adapted to be rotated by a given angle by the rotary force of the rotary member transmitted from the protrusion; and an ejection cap disposed on the output side of the ejection cam and having a groove into which the blood collection needle is inserted formed at the inside thereof so as to escape the blood collection needle from the insertion groove by the rotary force of the ejection cam.

26. The automated blood collection device according to claim 25, wherein the ejection cap is adapted to receive the rotary force of the ejection cam thereto and to escape the blood collection needle from the insertion groove so as to eject the blood collection needle used for the blood collection to the outside.

27. The automated blood collection device according to claim 26, further comprising a stopper fixedly mounted along the fixing shaft so as to restrict a moving distance of the fixing part when the blood collection needle is fixed.

28. The automated blood collection device according to claim 27, wherein the fixing cam, the guide cam, the ejection cam and the conveying cam of the automated blood collection device have the form of a cam gear.

29. The automated blood collection device according to claim 28, wherein the fixing cam, the guide cam, the ejection cam and the conveying cam of the automated blood collection device have the form of a cam plate.

* * * * *